United States Patent [19]

Miyahara et al.

[11] Patent Number: 5,183,754
[45] Date of Patent: * Feb. 2, 1993

[54] METHOD FOR PRODUCTION OF HUMAN TISSUE TYPE PLASMINOGEN ACTIVATOR

[75] Inventors: Shoichiro Miyahara, Yokohama; Atsunori Shindo, Kamakura; Maki Suzuki; Nobumi Kusuhara, both of Yokohama; Nobuyoshi Makiguchi, Fujisawa, all of Japan

[73] Assignee: Mitsui Toatsu Chemicals, Incorporated, Tokyo, Japan

[*] Notice: The portion of the term of this patent subsequent to Sep. 29, 2009 has been disclaimed.

[21] Appl. No.: 412,818

[22] Filed: Sep. 27, 1989

[30] Foreign Application Priority Data

Oct. 4, 1988 [JP] Japan ................................ 63-249081
Dec. 16, 1988 [JP] Japan ................................ 63-316118

[51] Int. Cl.$^5$ .............................. C12N 9/64; C12N 9/48
[52] U.S. Cl. ..................................... 435/226; 435/212
[58] Field of Search ................ 435/212, 217, 215, 226

[56] References Cited

U.S. PATENT DOCUMENTS 3,732,146  5/1973  Heimbarger ........................ 435/217
4,600,580  7/1986  Smith .................................. 435/215
4,661,453  4/1987  Pollard ................................ 435/215
4,724,206  2/1988  Rupp et al. ...................... 435/240.22
4,740,461  4/1988  Kaufman ............................. 435/215
4,766,075  8/1988  Goeddel et al. ..................... 435/212
4,960,702  10/1990 Rice et al. ............................ 435/226

FOREIGN PATENT DOCUMENTS 0208486    1/1987  European Pat. Off. .
WO89/04867 6/1989  PCT Int'l Appl. .
2153830    8/1985  United Kingdom .

OTHER PUBLICATIONS

Grant et al, Thromb. Res. 40(3):393–400, 1985 in Biological Abstracts, vol. 81, No. 10, abstract 89439, 1986.

Primary Examiner—Douglas W. Robinson
Assistant Examiner—Mike Meller
Attorney, Agent, or Firm—Nixon & Vanderhye

[57] ABSTRACT

A method for the production of human tissue type plasminogen activator (human t-PA) using cells is disclosed. The method comprises producing the human t-PA in parallel with the growth of the cells or after the cells have been grown. To the cell culture bicarbonate ion is added at a concentration equivalent to 3 to 10 g/l of $NaHCO_3$ based on the true volume of the medium to increase the osmotic pressure of the medium to a range of 350 to 520 milliosmoles/liter.

4 Claims, No Drawings

METHOD FOR PRODUCTION OF HUMAN TISSUE TYPE PLASMINOGEN ACTIVATOR

BACKGROUND OF THE INVENTION

1. Field of the Invention

This invention relates to a method for producing tissue type plasminogen activator (hereinafter referred to as tPA), tPA which is produced and excreted by vascular endothelial cells and various tissue cells, lyses fibrin clots, namely thrombi. Thus, tPA is effective as a thrombolytic agent.

2. Description of the Prior Art

Various methods for producing tPA have already been suggested. An example of the representative methods is linking a DNA sequence of tPA to an appropriate promoter, recombining the sequence into an expression vector, transforming a host cell with the recombinant DNA sequence, cultivating the recombinant producing cell, thus transformed, in an appropriate medium to produce tPA, and then purifying the tPA using an affinity column and a gel-filtration column.

In such a method, examples of media for production of tPA generally include those containing inorganic acids, amino acids, vitamins, etc., such as Eagle Basal Medium (EMB), Eagle Minimum Essential Medium (EMEM), Dulbecco Modified Eagle Medium (DMEM) and RPMI 1640 medium, as basic components with supplementation of L-glutamic acid, 10% fetal calf serum (FCS) and sodium bicarbonate at a concentration of 1–2 g/liter to adjust the pH in the range 6.5–7.5.

For example, known methods include that in which Modified Eagle Medium supplemented with 10% fetal calf serum, sodium bicarbonate (1.2 g/liter) and an appropriate amount of L-glutamic acid is used for cultivation (Journal of Biological Chemistry Vol. 25, p. 7035) and that in whic cultivation is carried out in a basic medium such as DMEM, EMEM or PRMI 1640, supplemented with bicarbonate at a concentration less than 2.0 g/liter to adjust the pH in the range 6.5–7.5 (Japanese Patent Laid-Open No. 4233/1987).

According to the conventional methods described above, however, tPA production per unit cell number is extremely small and the productivity is poor so that the problems such as high production cost make them difficult to be applied for stable tPA production on a commercial scale.

On the other hand, it has been found recently that protein productivity by cells can be stimulated by increasing the osmotic pressure of the medium, although growth of the cells is slightly suppressed.

In general, in a process for producing a useful substance using animal cell cultivation, the conditions, such as osmotic pressure, pH and temperature, of the medium are controlled in extremely precise ranges. Particularly as to the osmotic pressure, it is controlled by modifying the composition of the medium in the range between 280 and 300 milliosmoles/liter which is the range equivalent to that of human blood and humor fluid or other body fluids.

In this regard, attempts have been made to improve productivity of a desired protein by increasing the osmotic pressure. For example, it is reported that in antibody production, the productivity of antibody producing cells is stimulated several times by increasing the amino acid concentration in the medium substantially to make the medium hypertonic up to 340 milliosmoles/liter (Japanese Patent Laid-Open No. 188062/1985).

However, the supplementation of amino acid to make the medium hypertonic may greatly influence cell metabolism, and in some cases the productivity of desired proteins may be adversely decreased.

The first object of the present invention is to provide a method in which the production of a desired protein, tPA, per unit cell number is improved. tPA has two molecular forms, single-chain tPA and double-chain tPA. Thrombolytic activity of double-chain tPA is higher than that of single-chain tPA. tPA has been conventionally developed as either the sole double-chain form or the mixture form of the double-chain and the single-chain form.

Double-chain tPA has high fibrinolytic activity, and it is highly possible that double-chain tPA activates plasminogen not in thrombi, where fibrinolytic effect is expected, but in the blood stream, which often causes clinical bleeding (Japanese Patent Laid-open Pub. No. 118717/1984).

However, single-chain tPA, which is considered to be a precursor of double-chain tPA, has high affinity to fibrin and is quickly converted to double-chain tPA once bound to fibrin.

Accordingly, single-chain tPA exhibits maximal plasminogen activity at clotting sites.

Thus, thrombolytic activity of single-chain tPA is relatively low and not exhibited in the blood stream. In consequence, for clinical use, single-chain tPA is in greater demand than double-chain tPA, and an effective method for the production of single-chain tPA is thus desired.

Known methods for preparing only single-chain tPA include a method in which cultivation and subsequent processing steps are carried out in the presence of aprotinin (European Patent Publication No. 41766), a method in which trypsin inhibitor or aprotinin is added in the culture medium for tPA-producing cells (Japanese Patent Laid-open Pub. No. 118717/1984), a method in which cultivation or induction production is carried out in a medium supplemented with aprotinin or benzamidine (Japanese Patent Laid-Open Pub. No. 19486/1986) and a method in which aprotinin or 6-aminocapronic acid is added in a purification process (Biochem. Biophys. Acta 719(2), 318–328, 1982). However, since aprotinin to be used is quite expensive, practical application on industrial scale is difficult. Consequently, a method in which low-molecular-weight chemicals are added in the place of expensive aprotinin derived from serum, namely, the methods in which antiplasmin agents such as epsilon-aminocapronic acid and tranexamic acid are added to the medium has been proposed (Japanese Patent Laid-Open Pub. No. 4233/1987).

However, significant promotion of the productivity of single-chain tPA is not accomplished by replacing aprotinin with low-molecular-weight antiplasmin agents or p-aminomethyl benzoic acid derivatives.

The second object of the present invention is to provide a method for improving the productivity of single-chain tPA to large extent.

SUMMARY OF THE INVENTION

In the course of intensive study to accomplish the objects of the present invention, the present inventors found that in tPA production, tPA productivity can be much improved by increasing the osmotic pressure of the medium up to 350 milliosmoles or more/liter by using bicarbonate ion.

Furthermore, the present inventors found that in tPA production, productivity of single-chain tPA can be much improved by adding low-molecular-weight antiplasmin agents in the medium in which the osmotic pressure is increased with bicarbonate ion up to 350 milliosmoles or more/liter, and thus completed the present invention.

Namely, the present invention relates to a method of producing human tissue type plasminogen activator, in which the osmotic pressure of the medium is increased using bicarbonate ion up to 350 milliosmoles or more/liter.

Furthermore, the present invention relates to a method of producing human tissue type plasminogen activator, in which productivity of single-chain tPA can be considerably improved by adding low-molecular-weight antiplasmin agents to the medium in which the osmotic pressure is increased using bicarbonate ion up to 350 milliosmoles or more/liter, tPA production according to the present invention can be carried out either in a parallel step simultaneously with cell growth or in a separate step independently from the cell growth.

According to the present invention, by increasing the osmotic pressure of the cell culture medium or tPA producing medium using bicarbonate ion up to 350 milliosmoles or more/liter, productivity of tPA can be much improved. Furthermore, due to the synergistic effect of bicarbonate ion and an antiplasmin agent added to the medium, productivity of single-chain tPA can be highly improved.

Further, in regard to the effect of the osmotic pressure of tPA producing medium, a technique in the presence of p-aminomethyl benzoic acid derivatives has been disclosed by the present inventors in their earlier patent application U.S. Ser. No. 07/247,649. (EP Appln. 89 304944.5).

DETAILED DESCRIPTION AND THE PREFERRED EMBODIMENTS

Bicarbonate ion used in the present invention to increase osmotic pressure can be provided in a medium as bicarbonates, e.g. sodium bicarbonate ($NaHCO_3$), potassium bicarbonate and calcium bicarbonate, which generate bicarbonate ion when incorporated in the medium, or as carbon dioxide gas at a concentration such that bicarbonate ion is dissociated when the gas is dissolved in water in the medium. Preferably, bicarbonates are used to obtain the desired concentration of bicarbonate ion, and, if necessary, carbon dioxide gas is introduced for subsequent adjustment, since the yield of bicarbonate ion generation is higher with the addition of bicarbonate than with the introduction of carbon dioxide gas.

tPA production may be carried out in the cell culture medium simultaneously with cell growth (one-step process) or in a separate in tPA producing medium independently from culture medium (two-step process). In the present invention, the procedure to increase the osmotic pressure of the medium by bicarbonate ion is effectively carried out on the relevant medium for tPA production. Namely, the procedure with bicarbonic ion is carried out on the cell culture medium in the case of the one-step process and on the tPA producing medium in the case of the two-step process. tPA production is greatly improved by these processes. Further, the term "medium" as used by itself in this specification means a medium related to tPA production.

An example of the cell culture medium in the present invention is a basal medium supplemented with fetal calf serum in an appropriate amount (0 to 10%), and further substances necessary for the cell growth, such as surfactants, amino acids, sugars and salts, if desired.

Furthermore, the tPA producing medium in the present invention is, for example, a basal medium supplemented with fetal calf serum in an appropriate amount (0 to 10%) and with tPA inducing substances such as zinc, cadmium and salts thereof at a concentration of 1 to 10 $\mu M$.

The basal medium in the present invention is a medium comprising, for example, amino acids, vitamins and inorganic salts. Examples of the basal medium include Dulbecco's Modified Eagle Medium (DMEM) (Nissui Pharmaceutical Co., Ltd.), 199 medium (Nissui Pharmaceuticals Co., Ltd.) and Eagle's Minimal Essential Medium.

According to the present invention, bicarbonate ion is used generally in such an amount as to make the sum of the osmotic pressure attributed to the supplemented inorganic salts, amino acids, vitamins and the like added to the medium and that attributed to the bicarbonate ion, 350 milliosmoles or more/liter. For example, when the osmotic pressure attributed to organic slats, amino acids or vitamins is 280 milliosomoles/liter, bicarbonate ion to provide further 70 milliosmoles or more/liter of osmotic pressure is added so as to total 350 milliosmoles or more/liter. However, in the case where the osmotic pressure totals 350 milliosmoles or more/liter, the osmotic pressure attributed to bicarbonate ion is preferably 70 milliosmoles or more/liter and more than 20% of the total. Namely, in order to make the osmotic pressure 350 milliosmoles/liter, the osmotic pressure of the medium should be less than 350 milliosmoles/liter without an addition of bicarbonate ion. Marked improvement in tPA productivity cannot be expected when additional bicarbonate ion is supplied to the medium in which osmotic pressure is already 350 milliosmoles or more/liter due to the addition of amino acids, etc., because the cell metabolism is being influenced by the hypertonic condition resulting from the amino acids, etc.

Namely, according to the present invention the osmotic pressure of a tPA producing medium is controlled using bicarbonate ion at 350 milliosmoles or more/liter, preferably in the range 350-1000 milliosmoles/liter, more preferably in the range of 350-500 milliosmoles/liter.

Excessively high osmotic pressure interferes with the growth of the cells. However, the interference is small as compared to that due to the osmotic pressure increased by other solutes.

In order to prevent suppression of cell growth due to increase in the osmotic pressure, the two step process in which cell growth and tPA production proceed separately may be preferable to the one-step process.

In order to control the osmotic pressure of the medium as above-mentioned, for example, sodium bicarbonate ($NaHCO_3$) at a concentration of more than about 3 g/liter, preferably at 3 to 12 g/liter is generally added to the medium. Sodium bicarbonate is more effective than other bicarbonates.

Means of addition and forms of bicarbonate ion are selected depending on the cultivation methods used. For example, when a T-flask, a roller bottle or the like is used, sodium bicarbonate is preferably added to the medium to make the osmotic pressure of the medium 350 to 500 milliosmoles/liter (about 3–12 g/liter of sodium bicarbonate).

Cultivation of cells and production of tPA are preferably carried out in a carbon dioxide gas incubator in either closed or open systems. Further, the amount of carbon dioxide gas dissolved in the medium under the 5% carbon dioxide gas atmosphere is at most about 0.001M which corresponds to about 1 milliosmole/liter. Thus, the overall influence of the atmospheric carbon dioxide gas is negligible in the medium at pH 6.5 to 7.5, the pH ranges used in practice for cultivation. The amount of carbon dioxide gas produced by cells is minute and negligible. On the other hand, when cultivation is carried out in a spinner or a jar, bicarbonate ion can be provided by supplying sodium bicarbonate in the medium prior to cultivation and also by blowing a controlled amount of carbon dioxide gas at a specified concentration into the system for production of tPA, so as to maintain the total osmotic pressure in the system at 350 to 500 milliosmoles/liter.

As described above, tPA productivity can be greatly improved by increasing the osmotic pressure of the medium using bicarbonate ion. Furthermore, according to the present invention, it is possible to selectively produce predominantly single-chain tPA which is extremely useful for clinical use, by adding low-molecular-weight antiplasmin agents to the medium.

Examples of low-molecular-weight antiplasmin agents to be used according to the present invention include 4-aminobutanoic acid, 5-aminopentanoic acid, 6-aminohexanoic acid and trans-4-(aminomethyl)cyclohexanecarboxylic acid (tranexamic acid). Other substances which have antiplasmin activity and have a molecular weight in the range 50–1000 can also be used. These compounds can be used also in forms of esters, metal salts such as alkali metals, or salts of acids such as chlorides. According to the present invention, low-molecular-weight antiplasmin agents are added at concentrations ranging from $10^{-4}$ to $10^{-1}$M, more preferably from $10^{-3}$ to $10^{-2}$M.

Further, antiplasmin agents are added to the cell culture medium in the one-step process and to the tPA producing medium in the two-step process. They may be added either during preparation of the medium or after making the medium hypertonic using bicarbonate ion.

An example of the tPA producing strain to be used in the present invention is hT-382 cell line (Japanese Patent Laid-Open Pub. No. 126978/1987) which is obtained by transforming mouse C-127 cells with the plasmid constructed with insertions both of a part of the BPV-derived plasmid and a part of pBR322 plasmid with incorporation of a DNA sequence in which a DNA sequence coding for human tissue type plasminogen activator derived from normal human cells is bound to a human-derived metallothionein promoter, and of a DNA sequence necessary to stop transcription.

Another example of the tPA producing strain is SV-21-M2.5 K7 cell line (Japanese Patent Laid-Open Pub. No. 126978/1987) which is obtained by transforming CHO (Chinese hamster ovary) cells with the plasmid comprising a DNA sequence in which a DNA sequence coding for human tissue plasminogen activator derived from normal human cells is bound to SV-40 early promoter and a DNA sequence coding for dihydrofolate reductase, and further by selecting cells carrying amplified genes on a medium supplemented with methotrexate. Naturally, any kind of tPA producing cells, for example, those produced in combination with other means such as mutation or adaptation, or those transformed by viruses may be used.

For cell cultivation and tPA production, any of the known methods are applicable. For example, the present invention can be accomplished for effective production of tPA, particularly of single-chain tPA, by using one of following known methods in combination with the process for making the medium hypertonic using bicarbonate ion or for adding an antiplasmin agent as described above.

As an illustration, an appropriate amount of cells are inoculated in a cell culture medium, optionally supplemented with a tPA inducer, in a T-flask and then incubated at an appropriate temperature for an appropriate time in a carbon dioxide gas incubator for tPA production in parallel with cell growth.

Alternatively, cells are inoculated in a cell culture medium in a T-flask and then allowed to grow at an appropriate temperature for an appropriate time in a carbon dioxide gas incubator. When the cells have grown to confluency, the medium is replaced by a tPA producing medium and then incubation is continued in the carbon dioxide gas incubator at an appropriate temperature for an appropriate time for tPA production.

For example, when a 75-cm$^2$ T-flask is used, cells are inoculated at a concentration of 0.5 to $2.0 \times 10^5$/ml and incubated at 37° C. for 3 to 4 days for growth in parallel with tPA production.

Alternately, for example, when a 75-cm$^2$ T-flask is used, cells are inoculated at a concentration of 1 to $2 \times 10^5$/ml and incubated at 37° C. for 3 to 4 days for cell growth. Then, the medium is replaced by a tPA producing medium, and the incubation is continued at 37° C. for 1 to 3 days for tPA production.

Furthermore, the present invention can be accomplished by using a spinner flask in the same manner.

Analysis of the tPA obtained by these methods according to the present invention revealed that the production was well over 10–30 mg/liter (as single-chain tPA) in the case where the osmotic pressure was 350 milliosmoles or more/liter, and in the case where an antiplasmin agent is added, the production of single-chain tPA particularly predominated. Production was 20 to 40 mg/liter, and 0 to 2 mg/liter for single-chain tPA and double-chain tPA, respectively, and the amount of single-chain tPA reached more than 95% of the total.

EXAMPLES

The present invention will be described more specifically by the following Examples:

The method for the analysis of single-chain tPA and double-chain tPA in the culture is as follows.

(1) Monoclonal antibodies to single-chain tPA (PAM-1, American Diagonotica Co.) and monoclonal antibodies to single-chain tPA plus double-chain tPA (PAM-2, American Diagonotica Co.) are diluted with a coating solution to 10 micrograms/ml, and 50 microliters each of the diluted solutions is dispensed into the wells of an ELISA plate (96 wells, Corning Glass Works). The plate is allowed to stand for 2 hours at room temperature, and then the fluid in the wells is discarded.

(2) Each of the wells is washed with a washing solution, and then filled with a blocking solution. The plate is allowed to stand for 30 minutes at room temperature.

Fifty microliters each of 1000- to 2000-fold diluted sample solutions and standard solutions (0, 1, 2, 4 and 8 ng/ml) are added into each of the wells, and the plate is allowed to stand for 2 hours.

(3) Each of the wells is again washed with the washing solution, and then an anti-tPA rabbit antibody is added to each well.

(4) Each of the wells is again washed with the washing solution, and then 50 microliters of a 500-fold diluted solution of goat anti-rabbit IgG and alkaline phosphatase conjugate (Sigma) is added to each well. The plate is allowed to stand for 1 hour.

(5) Each of the wells is again washed with the washing solution, and then 50 microliters of a substrate solution (p-nitrophenyl phosphate, Sigma) is added to each well. The plate is allowed to stand for 30 minutes.

(6) Fifty microliters of a 3N NaOH solution is added to each of the wells to stop enzymatic reaction.

(7) Absorption at 405 nm is read with a commercially available ELISA reader.

(8) A measuring line is drawn using the readings of standards, and the tPA concentrations in the samples are determined.

(9) Calculations are made as follows.

| | |
|---|---|
| Single-chain tPA content (mg/l) = | Measurement for PAM-1 |
| Double-chain tPA content (mg/l) = | Measurement for PAM-2 − measurement for PAM-1 |

Furthermore, the osmotic pressure was measured using a Shimazu Osmometer OSM-1 after sampling the fluids.

EXAMPLE 1

The cells used for tPA production were those of the above-mentioned hT-382 strain.

In 75-cm$^2$ T-flasks, 20 ml of each of Dulbecco's Modified Eagle Medium (DMEM) supplemented with 10% fetal calf serum which had been heat-inactivated and 10 $\mu$M zinc chloride was placed. To each medium, aprotinin (40 KIU) or tranexamic acid ($10^{-2}$M) and additionally sodium bicarbonate at the concentration shown in Table 1 were added. Each culture medium thus prepared was inoculated with the abovementioned cells at a concentration of $1.0 \times 10^5$ cells/ml.

The cells were incubated in the medium at 37° C. for 4 days in a 5% carbon dioxide gas incubator. When the cells were grown to confluency (about $10 \times 10^5$ cells/ml), concentrations of single-chain tPA and double-chain tPA in the culture were determined by the analysis described above. The results are shown in Table 1.

Further, the values given for the osmotic pressure were those measured when sodium bicarbonate was nearly completely ionized.

As shown in Table 1, tPA productivity in the culture in which the osmotic pressure was increased with NaHCO$_3$ was improved independently of the addition of either aprotinin or tranexamic acid.

Furthermore, the improvement in tPA productivity was remarkable when tranexamic acid was added; particularly, the production of single-chain tPA was highly improved.

TABLE 1

| NaHCO$_3$ (g/l) | Osmotic pressure (m osm) | Additive | sc-tPA* (mg/l) | sc-tPA rate (%) | Note |
|---|---|---|---|---|---|
| 1.0 | 300 | AP** | 6.4 | 90 | Normal medium |
| | | TKA*** | 7.4 | 94 | |
| 5.0 | 380 | AP | 10.2 | 92 | |
| | | TKA | 22.1 | 96 | |
| 7.5 | 450 | AP | 14.3 | 92 | |
| | | TKA | 24.3 | 97 | |
| 10.0 | 520 | AP | 7.4 | 90 | *4 |
| | | TKA | 12.6 | 95 | |

*Single-chain tPA
**Aprotinin
***Tranexamic acid
*4The pH of the medium exceeded 8 and cell growth was slightly suppressed.

EXAMPLE 2

The cell line used in Example 1 was similarly used. The cells were inoculated at a concentration of $1.0 \times 10^5$ cells/ml in 20 ml each of Dulbecco's Modified Eagle Medium (DMEM) supplemented with 10% heat-inactivated fetal calf serum in 75-cm$^2$ T-flasks.

The cells were incubated at 37° C. for 4 days in a carbon dioxide gas incubator. When the cells were grown to confluency (about $10 \times 10^5$ cells/ml), the medium was discarded and then replaced with 20 ml of the tPA producing medium having the same composition as described above except that zinc chloride at a concentration of 10 $\mu$M and aprotinin (40 KIU) or tranexamic acid ($10^{-2}$ M) and the further additives as specified in Table 2 were supplemented. Incubation was continued in a carbon dioxide gas incubator at 37° C. for 2 days. The concentrations of single-chain tPA and double-chain tPA in the culture were determined as described in Example 1. Results are shown in Table 2.

As shown in Table 2, the results using the various tPA producing media were similar to those obtained in Example 1. Furthermore, the tPA production was itself generally improved since the tPA producing medium was used.

TABLE 2

| NaHCO$_3$ (g/l) | Osmotic pressure (m osm) | Additive | sc-tPA* (mg/l) | sc-tPA rate (%) | Note |
|---|---|---|---|---|---|
| 1.0 | 300 | AP** | 8.6 | 90 | Normal medium |
| | | TKA*** | 9.2 | 95 | |
| 5.0 | 380 | AP | 24.3 | 88 | |
| | | TKA | 32.0 | 93 | |
| 7.5 | 450 | AP | 32.0 | 92 | |
| | | TKA | 41.3 | 94 | |
| 10.0 | 520 | AP | 21.0 | 94 | |
| | | TKA | 28.5 | 94 | |

*Single-chain tPA
**Aprotinin
***Tranexamic acid

EXAMPLE 3

The cells used for tPA production were those of SV-21-M2.5 K7 cell line.

The tPA production was carried out in the same manner as described in Example 1 except that zinc chloride was not added to the medium. The results are shown in Table 3.

As evident in Table 3, a similar effect as shown in Example 1 was observed also with this particular cell line.

TABLE 3

| NaHCO$_3$ (g/l) | Osmotic pressure (m osm) | Additive | sc-tPA* (mg/l) | sc-tPA rate (%) | Note |
|---|---|---|---|---|---|
| 1.0 | 300 | AP** | 3.4 | 93 | Normal medium |
|  |  | TKA*** | 3.6 | 92 |  |
| 5.0 | 380 | AP | 8.2 | 88 |  |
|  |  | TKA | 16.2 | 92 |  |
| 7.5 | 450 | AP | 10.4 | 92 |  |
|  |  | TKA | 20.0 | 94 |  |
| 10.0 | 520 | AP | 7.5 | 90 |  |
|  |  | TKA | 15.4 | 90 |  |

*Single-chain tPA
**Aprotinin
***Tranexamic acid

TABLE 4

| Osmotic pressure (milliosmoles) | Additive | Single-chain tPA (mg/ml) | | | | | Total |
|---|---|---|---|---|---|---|---|
|  |  | 1 | 2 | 3 | 4 | 5 |  |
| 300 | AP* | 4.3 (87) | 6.2 (88) | 7.7 (91) | 4.8 (90) | 4.0 (88) | 27.0 |
|  | TKA** | 5.0 (92) | 6.0 (94) | 7.6 (91) | 5.4 (93) | 4.2 (95) | 28.2 |
| 380 | AP | 5.3 | 10.4 | 12.8 | 14.2 | 11.3 | 54.0 |
| 450 | AP | 10.1 (90) | 13.4 (89) | 17.2 (93) | 16.8 (92) | 12.2 (91) | 69.7 |
|  | TKA | 8.2 (93) | 18.0 (93) | 24.2 (96) | 28.3 (94) | 34.0 (92) | 112.7 |
| 520 | AP | 6.4 | 9.8 | 12.2 | 15.3 | 14.2 | 58.7 |

Rates of single-chain tPA (%) were given in parentheses.
*Aprotinin
**Tranexamic acid

EXAMPLE 4

The cells used for the tPA production were those of the same strain as used in Example 1. The cells (10$^8$ cells) were inoculated at a concentration of 1.0×10$^5$ cells/ml in 1 liter each of DMEM supplemented with 10% heat-inactivated fetal calf serum in 1-liter spinner flasks (total capacity of about 1.5 liter) each equipped with stirring blades, pH electrodes, DO electrodes and a pipe for introducing gas. Seed cells used had been cultured in advance in the abovementioned medium in a roller bottle. Incubation was carried out at 37° C. for 4 days. When the cell concentration reached 10$^6$ cells/ml, the abovementioned medium was discarded and replaced for tPA production with 1 liter each of DMEM supplemented with 5% heat-inactivated fetal calf serum, aprotinin (40 KIU/ml) or tranexamic acid (10$^{-2}$ M) and zinc chloride (10 μM) and further sodium bicarbonate (5.0 g/liter).

In order to maintain the osmotic pressure of the medium as shown in Table 4, 5% carbon dioxide gas was occasionally blown into the bottle. pH was adjusted with NaOH. Further, DO was maintained at 1 PPM and the temperature at 37° C. Medium changes were carried out once a day for 5 days, thus tPA fractions were recovered totally five times.

As shown in Table 4, similar effects as shown in Example 1 was observed when the osmotic pressure was controlled by blowing carbon dioxide gas into the medium.

What is claimed is:

1. A method for producing human tissue type plasminogen activator using cells, wherein the human tissue type plasminogen activator is produced in parallel with growth of the cells in a cell culture medium in which bicarbonate ion equivalent to 3 to 10 g/l of NaHCO$_3$ based on the true volume of the medium is supplied to said cell culture medium to increase the osmotic pressure of the medium to a range of 350 to 520 milliosmoles/liter.

2. A method for producing human tissue type plasminogen activator using cells, wherein the cells are grown in advance in a medium and then incubated in a medium for the production of human tissue type plasminogen activator, the osmotic pressure in said medium for production of human tissue type plasminogen activator being increased using bicarbonate ion equivalent to 3 to 10 g/l of NaHCO$_3$ based on the true volume of the medium is supplied to said medium to increase the osmotic pressure of the medium to a range of 350 to 520 milliosmoles/liter.

3. The method of claim 1 or 2, in which a low-molecular-weight antiplasmin agent is added to said medium in addition to the bicarbonate ion, so that the antiplasmin agent directly inhibits the conversion of single-chain tPA into double-chain tPA, whereby single-chain tPA with only minor amounts of double-chain tPA is produced.

4. The method of claim 3 in which said antiplasmin is selected from the group consisting of 4-aminobutanoic acid, 5-aminopentanoic acid, 6-aminohexanoic acid, trans-4-(aminomethyl)cyclohexanecarboxylic acid and trans-4-(aminoethyl)cyclohexanecarboxylic acid.

* * * * *